United States Patent [19]

Saida et al.

[11] 4,316,767
[45] Feb. 23, 1982

[54] PROCESS FOR CONCENTRATING AQUEOUS UREA SOLUTIONS

[75] Inventors: Toyoyasu Saida, Fujisawa; Takatatsu Shimokawa, Mobara; Yuzuru Yanagisawa, Mobara; Takashi Nagahama, Mobara; Koji Ishida, Mobara, all of Japan

[73] Assignees: Toyo Enginnering Corporation; Mitsui Toatsu Chemicals Incorporated, both of Tokyo, Japan

[21] Appl. No.: 186,058

[22] Filed: Sep. 11, 1980

[30] Foreign Application Priority Data

Sep. 14, 1979 [JP] Japan .................... 54/117370

[51] Int. Cl.³ ........................... B01D 1/22
[52] U.S. Cl. ................... 159/47 UA; 159/49; 159/16 R; 159/13 A; 564/73
[58] Field of Search ........... 159/13 A, 13 C, 16 R, 159/47 UA, 49, DIG. 10; 260/555 A, 555 B; 569/555 C

[56] References Cited

U.S. PATENT DOCUMENTS

| 2,367,695 | 1/1945 | Spiselman | 159/13 C |
|---|---|---|---|
| 2,933,527 | 4/1960 | Guyer et al. | 159/47 UA |
| 3,147,174 | 9/1964 | Cook | 159/47 UA |
| 3,405,689 | 10/1968 | Peterson | 159/13 A |
| 3,491,821 | 1/1970 | Graumann et al. | 159/47 UA |
| 3,822,192 | 7/1974 | Brown | 159/16 R |

*Primary Examiner*—Norman Yudkoff

[57] ABSTRACT

Disclosed is a process for concentrating aqueous urea solutions in which an aqueous urea solution is allowed to flow as a falling film in countercurrent contact with a stream of hot inert gas to concentrate it to 95–99% by weight and the aqueous urea solution so concentrated is then passed through a packed zone in cocurrent contact with a stream of hot inert gas to concentrate it to not less than 99.5% by weight.

4 Claims, 2 Drawing Figures

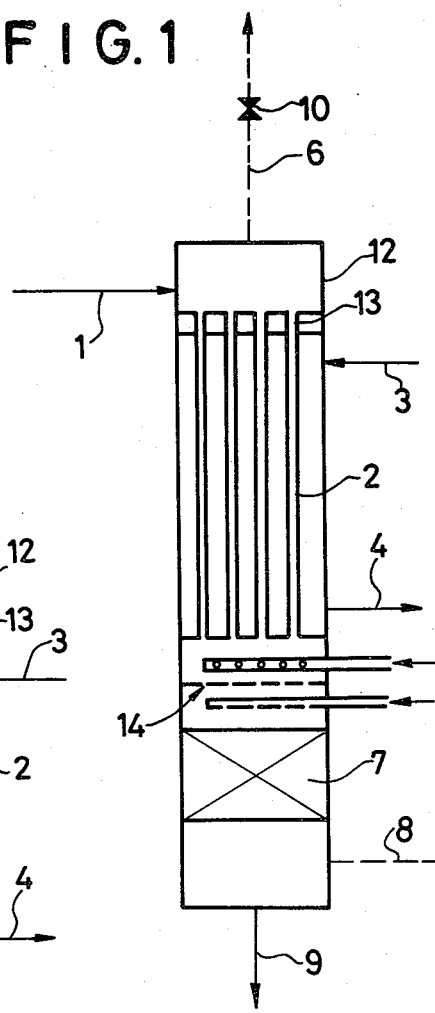
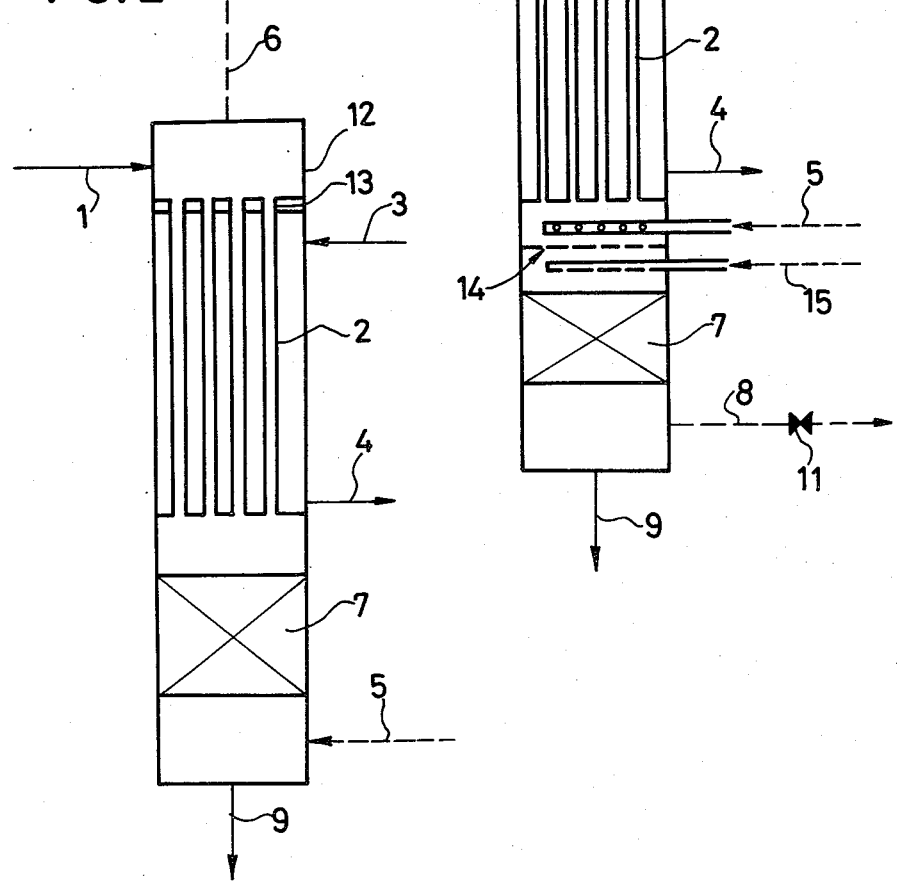

PROCESS FOR CONCENTRATING AQUEOUS UREA SOLUTIONS

BACKGROUND OF THE INVENTION

1. Field of the Invention

This invention relates to an improved process for concentrating aqueous urea solutions and, more particularly, to improvements in a two-step process for concentrating aqueous urea solution by use of a stream of hot inert gas.

2. Description of the Prior Art

An aqueous urea solution obtained by reacting ammonia and carbon dioxide at high temperature and pressure and subjecting the resulting urea synthesis effluent to conventional procedure for the removal of unreacted materials has a concentration of 70-90% by weight. Accordingly, in order to prepare granulated urea which is a common form of urea for practical use, this aqueous urea solution need be concentrated to not less than 99.5% by weight. There have been proposed a number of processes for effecting such concentration. As an example, U.S. Pat. No. 3,491,821 discloses a two-step process for concentrating aqueous urea solutions. More specifically, in the first step of this process, an aqueous urea solution having a concentration of 65-95% by weight is allowed to flow as a falling film along the interior surface of externally heated tubes and brought into countercurrent contact with a stream of hot inert gas, whereby it is concentrated to 97.5-99% by weight. In the succeeding second step, the aqueous urea solution resulting from the first step is passed through a packed zone in countercurrent contact with a stream of hot inert gas. (The stream of hot inert gas leaving the packed zone serves as the stream of hot inert gas used in the first step.)

However, in the process of U.S. Pat. No. 3,491,821 wherein an aqueous urea solution is brought into countercurrent contact with a stream of hot inert gas in the second step, blowing-up of the solution by the stream or back mixing of the solution due to blowing-up of its droplets by the stream occurs. Thus, the aqueous urea solution to be concentrated departs from the state of piston flow, so that the evaporation rate is decreased. (Supposing that this back mixing causes the aqueous urea solution passing through the concentrator to be in the state of complete mixing, the concentrator must be operated in such a way that the composition of the solution within the concentrator is equal to that of the solution at its outlet. Accordingly, the capacity for evaporating water from the solution will be minimized. Actually, the aqueous urea solution is presumed to be in an intermediate state between piston flow and complete mixing.) The influence of this back mixing becomes more marked in the concentration range of about 99% by weight and greater where the vapor pressure of water above the aqueous urea solution is sharply reduced as the concentration increases. Such a decrease in evaporation rate naturally prolongs the residence time in the apparatus (or packed zone). Consequently, the conversion of urea into biuret cannot be avoided and the size of the apparatus (or packed zone) need be increased in proportion to the prolonged residence time.

SUMMARY OF THE INVENTION

It is an object of the present invention to provide a two-step process for concentrating aqueous urea solutions by use of a stream of hot inert gas which can minimize the back mixing of the aqueous urea solution in the second step.

It is another object of the present invention to provide a two-step process for concentrating aqueous urea solutions which can decrease the formation of biuret.

These objects of the present invention are accomplished by a process for concentrating aqueous urea solutions which comprises the first step of letting an aqueous urea solution flow as a falling film in countercurrent contact with a stream of hot inert gas to concentrate the aqueous urea solution to 95-99% by weight and the second step of passing the aqueous urea solution resulting from the first step through a packed zone in cocurrent contact with a stream of hot inert gas to concentrate the aqueous urea solution to not less than 99.5% by weight.

BRIEF DESCRIPTION OF THE DRAWINGS

FIG. 1 is a schematic view illustrating one embodiment of the present invention; and FIG. 2 is a schematic view illustrating a prior art process as employed in the comparative examples which will be described later.

DETAILED DESCRIPTION OF THE INVENTION

The first step of the process provided by the present invention is carried out by means of a falling-film evaporator. For this purpose, any suitable falling-film evaporator (for example, one of the type that is disclosed in U.S. Pat. No. 3,491,821) and its well-known operating conditions may be employed. In the first step, an aqueous urea solution is concentrated from 70-90% by weight to 95-99% by weight.

The aqueous urea solution concentrated in the first step is then introduced into a concentrator including a packed bed, through which the aqueous urea solution is passed downward in cocurrent contact with a stream of hot inert gas and thereby concentrated to not less than 99.5% by weight. Preferably, the temperature of the stream of hot inert gas introduced into this second step is in the range of 140°-200° C. and the temperature of the aqueous urea solution introduced thereinto is in the range of 135°-160° C. It is particularly preferable that the concentration of the aqueous urea solution introduced into the second step is in the range of 98-99% by weight.

The packed bed 7 may be filled with any of the various well-known types of packings. Although the packing may be positioned either randomly or regularly, regularly positioned packings are particularly preferred because of the higher evaporation rate of water.

Now, one embodiment of the present invention is specifically described in connection with the accompanying drawings.

Referring to FIG. 1, an aqueous urea solution having a concentration of 70-90% by weight and a temperature of 90°-120° C. is fed from a urea purification system through a line 1 to the top of a concentrating apparatus 12. The aqueous urea solution so fed is evenly distributed among heat transfer tubes 2 with the aid of an inlet weir 13. As the aqueous urea solution flows as a falling film along the inner wall of the heat transfer tubes 2, it is heated with steam (having a pressure of 3.0-6.0 kg/cm$^2$) introduced through a line 3 and discharged as a drain through a line 4, and brought into countercurrent contact with a stream of hot inert gas (for example, air) introduced through a line 5, whereby it is concentrated to 95-99% by weight. The temperature of the aqueous urea solution leaving the heat transfer tubes 2 is preferably in the range of 135°-160° C. and more preferably in the range of 135°-150° C. The flow rate of the stream of hot inert gas introduced through the line 5 is preferably equal to 300-900 Nm$^3$/hr for each ton/hr of the aqueous urea solution fed through the line 1, and its temperature is preferably in the range of 150°-170° C.

The stream of hot inert gas accompanied by the resulting water vapor is discharged through a line 6 and a valve 10. If necessary, the stream of hot inert gas may be subjected to a suitable procedure for recovering the very small amount of urea contained therein and removing the very small amount of ammonia contained therein before it is discharged to the atmosphere.

The aqueous urea solution which has been concentrated in the heat transfer tubes 2 leaves the lower end of the heat transfer tubes 2, passes through a wire screen 14 (the mesh size of which is preferably such that a small amount of the aqueous urea solution is held thereon, though this wire screen can be omitted), and falls onto a packed bed 7. In this packed bed 7, the aqueous urea solution is brought into cocurrent contact with a stream of hot inert gas introduced through a line 15, whereby it is concentrated to not less than 99.5% by weight. The stream of hot inert gas introduced through the line 15 preferably has a dew point of 5° C. or below. Moreover, its flow rate is preferably equal to 200-500 Nm$^3$/hr for each ton/hr of the aqueous urea solution fed through the line 1, and its temperature is preferably in the range of 140°-200° C. and more preferably in the range of 150°-200° C. The resulting concentrate, which has a temperature of 135°-145° C., is recovered through a line 9 and fed to a granulating tower. The inert gas which has passed through the packed bed 7 is discharged through a line 8 and a valve 11. The valves 10 and 11 serve to regulate the flow rate of the streams of hot inert gas passing through the heat transfer tubes 2 and the packed bed 7, respectively.

According to the present invention, the back mixing of the aqueous urea solution in the second step is minimized, so that the formation of biuret is significantly decreased as is evident from the examples and comparative examples which will be given later. It is really surprising that such a remarkable effect is produced by altering the countercurrent contact of an aqueous urea solution with a stream of hot inert gas in the second step (as is the case with the aforementioned prior art process) to cocurrent contact. Moreover, this effect can further be enhanced by using a packed bed filled with a regularly positioned packing.

The present invention, together with the effects thereof, is more specifically explained with reference to the following examples and comparative examples. However, these examples are intended merely to illustrate the present invention and are not to be construed to limit the present invention.

EXAMPLES 1 and 2

Tests were carried out in a concentrating apparatus of the type illustrated in FIG. 1. As the heat transfer tubes 2 of this concentrating apparatus 12, 140 round tubes having an outside diameter of 51 mm, a wall thickness of 2 mm, and a length of 7.5 m were used. The packed bed 7 were filled with 1B Raschig rings. In Example 1, they were regularly positioned to a height of 0.3 m, while in Example 2, they were randomly positioned to a height of 0.6 m.

The other operating conditions and the test results are summarized in the Table given below.

COMPARATIVE EXAMPLES 1 and 2

Tests were carried out in a concentrating apparatus of the type illustrated in FIG. 2. In this figure, the parts corresponding to those shown in FIG. 1 are designated by the same reference numerals. The specifications for the heat transfer tubes 2 and the Raschig rings used in the packed bed 7 were the same as described in Examples 1 and 2. An inert gas, which was fed through a line 5 to the bottom of the apparatus, passed through the packed bed 7 and then through the heat transfer tubes 2 in countercurrent contact with an aqueous urea solution. Thereafter, it was discharged from the top of the apparatus through a line 6.

The other operating conditions and the test results are summarized in the following Table, together with those of Examples 1 and 2.

TABLE

| | Item | Example 1 | Example 2 | Comparative Example 1 | Comparative Example 2 |
|---|---|---|---|---|---|
| Apparatus | Heat transfer tubes | 140 tubes having an outside diameter of 51 mm, a wall thickness of 2 mm, and a length of 7.5 m | | | |
| | Type of packing | Raschig rings | Raschig rings | Raschig rings | Raschig rings |
| | Mode of filling | Regular | Random | Regular | Random |
| | Height of packed bed (m) | 0.3 | 0.6 | 0.3 | 0.6 |
| | Flow of aqueous urea solution and inert gas | Cocurrent | Cocurrent | Countercurrent | Countercurrent |
| Operating Conditions | Aqueous urea solution Concentration (wt. %) | 83 | 83 | 83 | 83 |
| | Biuret content (wt. %) | 0.43 | 0.43 | 0.43 | 0.43 |
| | Feed rate (tons/hr) | 6 | 6 | 6 | 6 |
| | Flow rate of inert gas Through heat transfer tubes (Nm$^3$/hr) | 3,000 | 3,000 | | |
| | Through packed bed (Nm$^3$/hr) | 2,000 | 2,000 | 4,100 | 4,100 |
| | Temperature of inert gas At inlet of heat transfer tubes (°C.) | 150 | 150 | 150 | 150 |

TABLE -continued

| Item | | Example 1 | Example 2 | Comparative Example 1 | Comparative Example 2 |
|---|---|---|---|---|---|
| Results | At inlet of packed bed (°C.) | 150 | 150 | 150 | 150 |
| | Steam pressure (kg/cm$^2$) | 3.5 | 3.5 | 3.5 | 3.5 |
| | Concentrate recovered from outlet of apparatus | | | | |
| | Concentration (wt. %) | 99.7 | 99.7 | 99.7 | 99.7 |
| | Biuret content (wt. %) | 0.68 | 0.70 | 0.80 | 0.83 |
| | Increase in biuret content (wt. %) | 0.25 | 0.27 | 0.37 | 0.40 |

What is claimed is:

1. In a process for concentrating aqueous urea solutions including a first step of letting an aqueous urea solution flow as a falling film in countercurrent contact with a first stream of hot inert gas to concentrate the aqueous urea solution to a concentration of 95-99% by weight and a second step of passing the aqueous urea solution resulting from the first step through a packed zone in contact with a second stream of hot inert gas to concentrate the aqueous urea solution to a concentration of not less than 99.5% by weight, the first and second steps being conducted at substantially atmospheric pressure, the improvement which comprises, in said second step, passing said second stream of hot inert gas having a temperature of 140°-200° C. in an amount of from 200 to 500 m$^3$/hr, measured at N.T.P., for each ton/hr of the aqueous urea solution fed into said first step, through the packed zone in cocurrent flow with said aqueous urea solution fed into said second step.

2. A process as claimed in claim 1 wherein the temperature of the aqueous urea solution introduced into the second step is in the range of 135°-160° C.

3. A process as claimed in claim 1 wherein the packed zone is filled with a regularly positioned packing.

4. A process as claimed in claim 1 wherein the stream of hot inert gas introduced into the second step has a dew point of 5° C. or below.

* * * * *